(12) United States Patent
Hiles et al.

(10) Patent No.: US 8,591,930 B2
(45) Date of Patent: Nov. 26, 2013

(54) GROWTH FACTOR MODIFIED EXTRACELLULAR MATRIX MATERIAL PREPARATION AND METHODS FOR PREPARATION AND USE THEREOF

(75) Inventors: Michael C. Hiles, Lafayette, IN (US); Andrew Brightman, West Lafayette, IN (US); Abram D. Janis, Valencia, CA (US)

(73) Assignee: Cook Biotech Incorporated, West Lafayette, IN (US)

( * ) Notice: Subject to any disclaimer, the term of this patent is extended or adjusted under 35 U.S.C. 154(b) by 1400 days.

(21) Appl. No.: 12/110,630

(22) Filed: Apr. 28, 2008

(65) Prior Publication Data
US 2008/0299171 A1 Dec. 4, 2008

Related U.S. Application Data

(60) Provisional application No. 60/914,485, filed on Apr. 27, 2007.

(51) Int. Cl.
*A61F 2/00* (2006.01)

(52) U.S. Cl.
USPC .................. 424/423; 424/574; 514/2; 514/12

(58) Field of Classification Search
None
See application file for complete search history.

(56) References Cited

U.S. PATENT DOCUMENTS

| | | | |
|---|---|---|---|
| 2,127,903 A | 5/1936 | Bowen | |
| 2,167,251 A | 7/1939 | Rogers | |
| 3,272,204 A | 9/1966 | Artandi et al. | |
| 4,321,914 A | 3/1982 | Begovac et al. | |
| 4,781,176 A | 11/1988 | Ravo | |
| 4,801,299 A | 1/1989 | Brendel et al. | |
| 4,902,508 A | 2/1990 | Badylak et al. | |
| 4,950,483 A | 8/1990 | Ksander et al. | |
| 4,956,178 A | 9/1990 | Badylak et al. | |
| 4,969,902 A | 11/1990 | Ravo | |
| 5,269,774 A | 12/1993 | Gray | |
| 5,281,422 A | 1/1994 | Badylak et al. | |
| 5,294,551 A | 3/1994 | Furcht et al. | |
| 5,554,389 A | 9/1996 | Badylak et al. | |
| 5,613,982 A | 3/1997 | Goldstein | |
| 5,955,110 A | 9/1999 | Patel et al. | |
| 6,099,567 A | 8/2000 | Badylak et al. | |
| 6,206,931 B1 | 3/2001 | Cook et al. | |
| 6,475,232 B1 | 11/2002 | Babbs et al. | |
| 7,871,440 B2 * | 1/2011 | Schwartz et al. | 623/14.12 |
| 7,887,576 B2 * | 2/2011 | Bahler et al. | 623/1.13 |
| 7,914,808 B2 * | 3/2011 | Malaviya et al. | 424/423 |

FOREIGN PATENT DOCUMENTS

| | | |
|---|---|---|
| EP | 1452153 | 9/2004 |
| EP | 1508613 | 2/2005 |
| WO | WO 9942126 | 8/1999 |
| WO | WO 2004/091370 | 10/2004 |
| WO | WO 2006008748 | 1/2006 |
| WO | WO 2006/044512 | 4/2006 |

OTHER PUBLICATIONS

Sakiyama et al. (FASEB J. vol. 13, pp. 2214-2224, 1999).*
Halstenberg et al. (Biomacromolecules, vol. 3, 2002, pp. 710-723).*
Lever et al. (Macmillan Magazine Ltd., vol. 1, 2002).*
Kanematsu et al. (Biomaterials, vol. 25, 2004, pp. 4513-4520).*
(Halstenberg et al. (Biomacromolecules, 2002, vol. 3, pp. 710-723).*
International Search Report in PCT/US2008/061727 dated Jul. 24, 2008.
Written Opinion in PCT/US2008/061727 dated Jul. 24, 2008.

* cited by examiner

*Primary Examiner* — Hope Robinson
(74) *Attorney, Agent, or Firm* — Woodard, Emhardt, Moriarty, McNett & Henry LLP

(57) ABSTRACT

Described are tissue graft constructs that include submucosa and other extracellular matrix materials that incorporate a number of exogenous proteins. Further described are methods for making tissue graft constructs that include stripping endogenous heparin binding proteins from a porcine graft material and thereafter binding one or more human growth factors to the native heparin molecules that are retained within the graft material. Such graft materials may be used in methods for the treatment of wounds in patients.

19 Claims, No Drawings

GROWTH FACTOR MODIFIED EXTRACELLULAR MATRIX MATERIAL PREPARATION AND METHODS FOR PREPARATION AND USE THEREOF

REFERENCE TO RELATED APPLICATION

The present application claims the benefit of U.S. Provisional Patent Application Ser. No. 60/914,485 filed Apr. 27, 2007, entitled GROWTH FACTOR MODIFIED EXTRACELLULAR MATRIX MATERIAL AND METHODS FOR PREPARATION AND USE THEREOF which is hereby incorporated by reference in its entirety.

BACKGROUND

The present invention relates generally to tissue graft materials, and in particular aspects to tissue graft constructs including a submucosa or other extracellular matrix material having exogenous growth factors bound thereto. Such materials are useful in wound care, such as in the treatment of chronic wounds, e.g. chronic ulcers.

As further background, wound healing is a complex process involving platelets, the immune system, the extracellular matrix, and various cytokines and growth factors. Wound healing generally occurs in four major phases: inflammation, cell proliferation, matrix deposition, and remodeling. Each stage of healing requires a specific group of extracellular signals to proceed. These extracellular signals can include the presence of growth factors and cytokines, whose order of release and concentrations are controlled during the healing response by cells in the wound. The type of growth factors and cytokines that participate in wound healing can vary depending on the species of the patient, the type of wound, and the wound's location.

Dermal wound healing is especially critical to maintaining the body's primary line of defense. The skin provides the body with a protective barrier from chemical and mechanical challenges, harmful pathogens, and ultraviolet radiation. Chronic wounds compromise the skin's ability to defend against these agents, due to the prolonged wound healing process.

For chronic wounds, the body is unable to complete the wound healing process due to compromised vascularization or immune system. Without clinical intervention, these chronic wounds can lead to the spread of infection, significant necrotic tissue, and possible amputation in the case of ulcers in the foot. Advanced states of chronic dermal wounds present a significant clinical challenge. In the United States alone, there are over 3 million cases of chronic wounds annually.

In view of this background, there remain needs for improved or alternative medical grafting materials, methods for manufacturing medical grafting materials, and methods for using medical grafting materials. The present invention is addressed to these needs.

SUMMARY OF THE INVENTION

Accordingly, in certain aspects, the present invention provides a tissue graft construct that includes a number of exogenous proteins bound to native heparin molecules within a collagenous graft material. In additional aspects, the exogenous proteins comprise a cocktail or selection of bioactive agents that can facilitate a desirable wound healing response in patient tissue. The tissue graft construct is formed by replacing heparin binding proteins within the graft material with non-native or exogenous proteins that will bind to the native heparin molecules.

In another aspect, the present invention provides a medical graft product that includes an extracellular matrix (ECM) material retaining native heparin molecules. The extracellular matrix material is substantially depleted of native heparin binding proteins and contains non-native heparin binding proteins that are bound to the native heparin molecules.

In yet another aspect, the present invention includes a medical product for healing a wound in a patient that includes an extracellular matrix material and one or more exogenous growth factors. The exogenous growth factors are bound to native heparin binding sites that are retained within the extracellular matrix material. In certain aspects, the extracellular matrix material is porcine submucosa and the exogenous growth factors are human growth factors.

In still yet another aspect, the present invention provides a medical product for facilitating the repair of patient tissue that includes a collagenous material having endogenous heparin molecules to which exogenous heparin binding proteins are bound. The exogenous heparin binding proteins are effective to facilitate tissue repair.

In another aspect, the present invention provides a medical graft product for tissue repair in a patient that includes a sterile, remodelable, and collagenous extracellular matrix material retaining native heparin molecules that is substantially depleted of native heparin binding proteins.

In yet another aspect, the present invention provides a method for preparing a medical graft material that includes providing an extracellular matrix material having native heparin molecules and thereafter treating the extracellular matrix material to remove native heparin binding proteins and prepare a modified extracellular matrix material. The method continues by contacting the modified extracellular matrix material with one or more exogenous heparin binding proteins so as to prepare a second modified extracellular matrix material having exogenous proteins bound to the native heparin molecules.

In still yet another aspect, the present invention provides a method for preparing a medical graft that includes contacting an extracellular matrix material with a heparin containing liquid medium so as to remove native heparin binding growth factors from the extracellular matrix material and form a modified extracellular matrix material having native available heparin binding sites. The method continues by contacting the modified extracellular matrix material with a liquid medium that contains one or more exogenous growth factors so as to bind the one or more exogenous growth factors to the native available heparin binding sites.

In another aspect, the present invention provides a method for treating a patient wound that includes contacting a patient wound with a remodelable extracellular matrix material that is substantially depleted of native heparin binding proteins but has native heparin molecules that are bound to exogenous heparin binding growth factors.

In yet another aspect, the present invention provides a medical kit that includes a medical product of the invention enclosed in sterile medical packaging. In certain aspects, the medical product includes an extracellular matrix material having native heparin molecules yet being substantially depleted of native heparin binding proteins. The extracellular matrix material contains non-native heparin binding proteins that are bound to the native heparin molecules.

In still yet another aspect, the present invention provides a medical product for repairing patient tissue that includes a collagenous remodelable material having native heparin molecules bound to non-native growth factors. The collagenous remodelable material is porcine and the non-native growth factors are human. Advantageous such collagenous remodelable materials include porcine extracellular matrix material, such as porcine small intestine submucosa.

In another aspect, the present invention provides a method for repairing a wound that includes providing a plurality of porcine ECM graft constructs. Each ECM construct includes a cocktail of human growth factors bound to native heparin molecules and each growth factor cocktail varies such that each ECM construct optimally promotes wound repair during different stages of wound healing. The method continues by applying each of the plurality of ECM constructs to a patient wound during different stages of wound healing so as to optimally facilitate the repair or healing of the patient's wound.

In yet another aspect, the present invention provides a method for treating a wound in a patient that includes providing a porcine ECM graft material that contains a cocktail of exogenous human growth factors bound to native heparin molecules, wherein the cocktail of human growth factors facilitates a healing response in patient tissue that surrounds a wound. The method continues by contacting the ECM graft material to the patient tissue that surrounds the wound so as to promote a healing response in the tissue and heal or treat the wound.

The present invention provides improved and/or alternative methods and systems for repairing patient tissue, as well as improved and/or alternative medical graft products. Additional embodiments as well as features and advantages of the invention will be apparent from the further descriptions herein.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, certain aspects of the invention provide a tissue graft construct that includes one or more exogenous proteins bound to native heparin molecules within a collagenous graft material, such as a porcine extracellular matrix (ECM) material. The exogenous proteins can include a cocktail of human growth factors that are selected to facilitate a desirable wound healing result in patient tissue once the graft is implanted. In certain embodiments, the tissue graft construct can be formed by stripping endogenous heparin binding proteins from an ECM material and thereafter binding a selected mixture of exogenous growth factors to the native heparin molecules within the ECM material.

Turning now to a discussion of remodelable materials that can be useful in forming tissue grafts of the invention, in certain aspects, tissue graft materials of the invention can incorporate a collagenous material, such as an ECM material and especially a submucosa material. Other ECM materials that may be used include renal capsule membrane, dermal collagen, dura mater, pericardium, serosa, peritoneum, or basement membrane. Preferred medical graft products of the invention will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

Processed, naturally-derived ECM materials of the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive components, the ECM material can retain these components interspersed as solids between, upon and/or within the collagen fibers. Particularly desirable naturally-derived ECM materials for use in the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The processed ECM material of the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

It is advantageous to prepare bioremodelable ECM materials for the medical graft products and methods of the present invention. Such materials that are bioremodelable and promote cellular invasion and ingrowth provide particular advantage. Bioremodelable materials may be used in this context to promote cellular growth within the site in which a medical graft material of the invention is implanted.

As prepared and used, the submucosa material or any other ECM material will retain proteins or other bioactive components native to the source tissues, such as heparin or heparin sulfate binding proteins. Illustrative such heparin or heparin sulfate binding proteins can include, for example, growth factors, such as acidic fibroblast growth factor (aFGF), basic fibroblast growth factor (bFGF), transforming growth factor beta (TGF-β), vascular endothelial growth factor (VEGF), endothelial growth factor (EGF), and/or the like. As well, submucosa or other ECM material used in certain embodiments of the invention may retain other biological materials such as hyaluronic acid, fibronectin, and the like. Thus, generally speaking, the submucosa or other ECM material may retain one or more bioactive components from the tissue source that can induce, directly or indirectly, a cellular response such as a change in cell morphology, proliferation, growth, protein or gene expression.

In another aspect, extracellular matrix graft materials can be prepared which have unique component profiles that are low in undesired components while retaining significant levels of desired components such as described in International PCT Application No. PCT/US07/82238, filed Oct. 23, 2007. These unique materials can be prepared by processing methods that comprise treating a relatively impure ECM starting material to decrease the content of the undesired components, such as nucleic acid, lipids and/or immunoglobulins such as IgA, while retaining substantial levels of desired components such as growth factor(s), proteoglycans and/or glycosaminoglycans (GAGs). Typically, the ECM starting material will be treated with a mild detergent solution, such as an ionic or nonionic detergent solution. The low concentration of detergent enables a retention of a substantial level of desired components, such as those as noted above. In certain modes of operation, the ECM material will be treated with an aqueous solution of sodium dodecyl sulfate (SDS) or another ionic or nonionic detergent at a detergent concentration of about 0.05% to about 1%, more preferably about 0.05% to about 0.3%. This treatment can be for a period of time effective to disrupt cell and nuclear membranes and to reduce the immunoglobulin (e.g. IgA) content of the ECM material, typically in the range of about 0.1 hour to about 10 hours, more typically in the range of about 0.5 hours to about 2 hours. Processing the isolated ECM material in this manner preferably disrupts cell and nuclear membranes and results in a material with a substantially reduced its IgA content, thus reducing the immunogenicity of the material. For example, a processed ECM material of the invention can have a native IgA content of no greater than about 20 µg/g. In preferred embodiments, an ECM material of the invention can have a native IgA content of no greater than 15 µg/g, no greater than 10 µg/g, or even no greater than 5 µg/g. In certain embodiments, the processed ECM material includes essentially no native IgA. By "essentially no IgA" is meant that the isolated ECM material includes IgA below detectable levels. Means for detecting IgA are well known in the art and include, for example, enzyme-linked immunosorbent assay (ELISA). It will be understood in this regard that ECM materials obtained from different sources may have differing immunoglobulins that predominate in the tissue. It is expected that the processing techniques disclosed herein will be effective to reduce the content of ECM materials in other immunoglobulins, including those that predominate in the source tissue. Accordingly, other aspects of the invention relate to the isolation of an ECM material that has substantially reduced levels (e.g. less than about 20 µg/g) of (i) the predominant immunoglobulin in the source tissue, or (ii) the total immunoglobulin content (the sum of all immunoglobulins in the tissue).

In addition to treating an ECM material with a detergent medium, the ECM material can be contacted with other agents that participate in achieving the desired ECM component profile. For example, the ECM material can be treated with an aqueous medium, preferably basic, in which DNA is soluble. Such a medium can in certain forms have a pH in the range of above 7 to about 9, with pH's in the range of about 8 to about 8.5 proving particularly beneficial in some embodiments. The basic aqueous medium can include a buffer, desirably a biocompatible buffer such as tris(hydroxymethyl)aminomethane (TRIS), and/or a chelating agent such as ethylene diamine tetraacetic acid (EDTA). In one preferred form, the nucleic acid solubilizing medium is a TRIS-borate-EDTA (TBE) buffer solution. In another preferred form, the nucleic acid solubilizing medium is a solution of ammonium hydroxide. This treatment with a DNA solubilizing medium can be for a period of time effective to reduce the DNA content of the ECM material, typically in the range of about 0.1 hour to about 10 hours, more typically in the range of about 0.5 hours to about 2 hours.

In addition to treatment with detergent and DNA-solubilization media, methods of preparing medical graft materials of the invention can involve treatment with a liquid medium that results in a substantial reduction of the level of lipid components of the ECM material. For example, the resulting native lipid content of the ECM material can be reduced to no greater than about 4% in certain embodiments. This can be accomplished, for example, by a preparative process that involves a step of treating the ECM material with a liquid organic solvent in which the lipids are soluble. Suitable such organic solvents include for example water-miscible solvents, including polar organic solvents. These include low molecular weight (e.g. $C_1$ to $C_4$) alcohols, e.g. methanol, ethanol, isopropanol, and butanols, acetone, chloroform, and others. Additional organic solvents include nonpolar solvents such as hexane, benzene, toluene and the like. In more preferred embodiments, the processed ECM material will be processed to have a native lipid content no greater than about 3%, or no greater than about 2.5%. This treatment with a lipid-removing medium can be for a period of time effective to reduce the lipid content of the ECM material, typically in the range of about 0.1 hour to about 10 hours, more typically in the range of about 0.1 hours to about 1 hours. In certain embodiments, multiple (two or more) such treatments will be conducted. Additionally, treatment with the lipid-reducing medium as discussed above can be carried out before or after treatment with a detergent medium and/or aqueous (preferably basic) DNA-reducing medium as discussed above. In certain preferred embodiments, treatment with the lipid-reducing medium will occur before treatment with the detergent medium and/or the aqueous (preferably basic) medium.

Further, in addition or as an alternative to the inclusion of such native bioactive components, non-native bioactive components such as those synthetically produced by recombinant technology or other methods, may be incorporated into the submucosa or other ECM material (such as is discussed herein for example). As is discussed below, these non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a premanufactured step, immediately prior to application (e.g. by soaking the material in a solution containing a suitable antibiotic such as cefazolin), or during or after application of the ECM material to the patient.

Submucosa or other ECM material used in certain embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in certain embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in certain embodiments of the present invention.

ECM materials used in the invention may be free of additional, non-native crosslinking, or may contain additional crosslinking. Such additional crosslinking may be achieved by photo-crosslinking techniques, by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

It is also possible for an ECM material used in the invention to comprise a multilaminate ECM material. To form a multilaminate material, two or more ECM segments are stacked, or one ECM segment is folded over itself at least one time, and then the layers are fused or bonded together using a bonding technique, such as chemical cross-linking or vacuum pressing during dehydrating conditions.

An adhesive, glue or other bonding agent may also be used in achieving a bond between ECM layers. Suitable bonding agents may include, for example, collagen gels or pastes, gelatin, or other agents including reactive monomers or polymers, for example cyanoacrylate adhesives. As well, bonding can be achieved or facilitated using chemical cross-linking agents, such as glutaraldehyde, formaldehyde, epoxides, genipin or derivatives thereof, carbodiimide compounds, polyepoxide compounds, or other similar agents, including those others identified in the discussions above. Cross-linking of ECM materials can also be catalyzed by exposing the matrix to UV radiation, by treating the collagen-based matrix with enzymes such as transglutaminase and lysyl oxidase, and by photocross-linking. The combination of one or more of these with dehydration-induced bonding may also be used.

A variety of dehydration-induced bonding methods can be used to fuse ECM portions of the bioremodelable material. In one preferred embodiment, the multiple layers of ECM material are compressed under dehydrating conditions. The term "dehydrating conditions" can include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Turning now to a discussion of exogenous molecules (i.e. those derived separately from the ECM material being treated) that can be useful in certain embodiments of the invention, illustrative such exogenous molecules can include any heparin or heparin sulfate binding molecule, or any combination thereof, whether isolated from naturally-occurring sources, or produced by recombinant DNA, or other synthetic techniques. In this regard, a variety of suitable bioactive molecules that bind to heparin or heparin sulfate are known. These include, for example, fibroblast growth factors (FGFs) such as FGF-1 (aFGF), FGF-2 (bFGF), FTF-3, FGF-4, FGF-5, FGF-6, FGF-7, FGF-8, and FGF-9; heparin binding epidermal growth factor (HBEFG); vascular endothelial growth factor (VEGF); vascular epithelial growth factor (VEG); connective tissue growth factor; heparin-binding growth associated molecule; placental growth factor (PlGF); heparin-binding EGF-like growth factor; transforming growth factor-beta (TFG-beta); interferon-gamma (IFN-gamma); platelet-derived growth factor (PDGF); pleiotrophin; platelet factor-4 (PF-4); interleukin-8 (IL-8); macrophage inflammatory protein-1 (MIP-1); interferon-γ-inducible protein-10 (IP-10); neurotrophine-6; midkine; adhesive matrix proteins such as fibronectin, vitronectin, laminin, collagens, and thrombospondin; serine protease inhibitors such as antithrombin III, heparin co-factor II and protease nexins; and tumor necrosis factor. Other bioactive molecules that bind heparin and/or heparin sulfate are also known and can be used within the scope of the present invention. Illustrative such heparin binding molecules are further discussed in U.S. Pat. No. 6,894,022 and/or U.S. patent application Ser. No. 11/735,215 entitled "Fibronectin-Modified ECM Tissue Graft Constructs and Methods for Preparation and Use Thereof," filed on Apr. 13, 2007.

One of the above referenced bioactive materials, or a plurality (two or more) of these biomaterials, may be incorporated into a modified ECM graft material. Heparin and heparin sulfate-binding growth factors, particularly those that promote or facilitate wound healing, provide a preferred set of exogenous bioactive materials for binding to endogenous heparin or heparin sulfate within the ECM material as discussed herein.

The exogenous growth factors and/or any other bioactive material used to modify the ECM material may each be from the same species of animal from which the ECM material was derived (e.g. autologous or allogenic relative to the ECM material) or may each be from a different species from the ECM material source (xenogenic relative to the ECM material). In certain embodiments, the ECM material will be xenogenic relative to the patient receiving the graft, and the added exogenous material(s) will be from the same species (e.g. autologous, allogenic, or synthetic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced. In preferred embodiments, the exogenous materials will be human growth factors and the ECM material will be porcine.

Turning now to a discussion of graft processing methods, illustrative tissue graft products of the invention can be formed by replacing the endogenous or native heparin binding proteins that are contained within a remodelable material with exogenous or non-native heparin binding proteins or other bioactive agents. In certain preferred embodiments, the endogenous heparin binding proteins of a porcine ECM material will be replaced by a selection or cocktail of human growth factors. The human growth factors and their concentrations within the graft construct can be customized to facilitate wound repair in a specific wound type and location. Tissue graft constructs containing differing growth factor cocktails can be applied to the same wound at different healing stages in order to better facilitate healing of the wound, if desirable.

Illustratively, endogenous heparin or heparin sulfate binding proteins can be removed from an ECM material by subjecting the ECM material to a solution that is effective to remove substantially all of the native heparin binding agents from the graft material, while substantially retaining the heparin molecules, as well as any non-heparin binding agents, bound within the graft construct. In preferred embodiments, the native heparin binding proteins can be removed by contacting the graft material with heparin molecules, such as a solution containing unfractionated heparin.

Material contacting can include any suitable means that promotes the release of heparin binding proteins into the solution. Illustrative such contacting conditions include soaking the construct in a bath containing the solution, spraying the graft material with a stripping solution, and/or the like. If desirable, the contacting solution can be replaced, cleaned, or refreshed during contacting and can also recirculate over the graft to facilitate molecule exchange. Illustratively, graft contacting can occur until an intermediate graft material is formed that is substantially depleted of native heparin or heparin sulfate binding agents, yet retains native heparin molecules bound within the graft material.

Illustrative tissue graft products of the invention can be formed by binding a number of exogenous bioactive agents to the free heparin binding sites contained within an intermediate graft product. Such binding can occur by placing the exogenous agents into a solution and thereafter contacting the solution with the intermediate graft material. The contacting can occur as discussed above, e.g. in a bath or via spray, as is desirable. In certain embodiments, the protein solution can contain a number of one specific protein, while in alternative embodiments, the solution can contain a mixture of two or more different proteins, in different ratios to modulate the properties of the resulting graft material, if desirable. Illustratively, for example, the solution can contain a ratio of selected human growth factors (a cocktail) that will bind to the intermediate graft material and that will promote or enhance the healing of a specific type of human tissue once the tissue graft is implanted within a patient.

In alternative embodiments, graft processing can occur through a dialysis or similar membrane, if desirable. For example, the dialysis membrane can separate an ECM material from the contacting solution during both native protein removal and exogenous protein binding. The membrane can be sized to provide for the passage of proteins of only certain size. Therefore, during endogenous protein removal, for example, the membrane will promote the retention of certain proteins within the intermediate and final graft construct by not allowing those proteins (whether heparin binding or not) to pass through the membrane and into the heparin extraction solution. During non-native protein binding, such as when the exogenous proteins are carried within a heparin solution, the membrane can further prevent dissociation and loss of certain native proteins within the graft construct while providing for the binding of the non-native proteins to the graft construct.

Tissue graft materials of the present invention may be provided in a variety of forms, including for example in sheet form, particulate form, or fluidized (e.g. injectable) form. Sheet forms may include openings such as perforations, holes or slits, which may provide benefit in a variety of tissue grafting applications including in wound care grafting applications. The tissue graft materials can be in their final physical form or in a precursor form during treatment with a stripping solution, exogenous proteins, and/or other exogenous bioactive molecules as disclosed herein. For example, a sheet of ECM material can be treated to have bound non-native heparin binding proteins. Subsequent modifications can include forming openings in the material as discussed above, or reducing the sheet material to particulate or fluidized (e.g. injectable) form. On the other hand, a sheet of ECM material can first be modified with openings or to provide a particulate or fluidized form, and then modified to either strip the endogenous heparin binding proteins or incorporate the non-native proteins. Still further, endogenous proteins may be removed from the ECM material in sheet form, and exogenous proteins added after modification of the sheet form e.g. to create openings, a particulate form, or a fluidized form. As those skilled in the art will appreciate, these and other modification techniques will be suitable for the present invention.

Additionally, in certain embodiments, the exogenous bioactive agents can be added to the intermediate product before the product is stored or packaged, i.e. as a pre-manufactured step, or, alternatively, intermediate graft products can be stored or packaged, and bioactive agents can then be bound to the graft construct at a later time, such as before packaging the final product or before implantation of the graft material in a patient, such as when the intermediate product and bioactive agents are packaged separately.

In certain inventive embodiments, a modified ECM in accordance with the invention is provided in a meshed form. Thus, the ECM medical graft product will have multiple slits therein to provide the mesh pattern, and in turn the mesh pattern will provide deformability to the collagen-containing layer, for example exhibiting an expansion ratio of at least about 1.2:1 when hydrated. These constructs will provide particular advantage in the treatment of externally exposed wounds such as burn wounds or ulcers of the skin.

Meshed and other medical graft constructs of the invention may include for example a single ECM layer or may include a plurality (two or more) of ECM layers. Preferred single- or multiple-layer ECM constructs of the invention will have an overall thickness of at least about 50 microns, typically ranging from about 80 to about 1000 microns, and in certain embodiments ranging from about 100 to about 1000 microns. Relatively thick constructs, such as multiple layered ECM constructs, can provide particularly advantageous and lasting collagen scaffolds for tissue ingrowth, especially in the field of wound care such as burn and ulcer care.

Meshed constructs of the invention will have a plurality of slits therein to provide a mesh pattern, and the mesh pattern will provide deformability to the structure, especially expandability. In this regard, in the preferred meshed constructs, expansion or other deformation of the meshed structure will widen the openings created by the slits of the mesh pattern, by lateral and/or vertical displacement of the edges of the slits relative to one another. Preferred devices of the invention will have a mesh pattern providing an expansion ratio of at least about 1.2:1 when the layer is completely hydrated, more preferably at least about 2:1, and most preferably at least about 3:1.

Medical graft devices of the invention can be used in grafting applications for treatment of human or other animal conditions. In one preferred application, the materials of the invention are used in the treatment of wounds and in particular open, cutaneous wounds. Open, cutaneous wounds may be classified into one of four grades depending on the depth of the wound. A Grade I wound is limited to the epithelium. A Grade II wound extends into the dermis. A Grade III wound extends into the subcutaneous tissue; and, a Grade IV wound (or full-thickness wound) exposes bone. The term "partial thickness wound" refers to wounds that encompass Grades I-III; examples of partial thickness wounds include burn wounds, pressure sores, venous stasis ulcers, and diabetic ulcers. Advantageous applications of products of the invention include the treatment of partial thickness open cutaneous wounds, including burns and ulcers. These wounds are often chronic (e.g. lasting at least about 30 days untreated), and benefit significantly from the application of graft products of the present invention.

In use for wound care, the physician, veterinarian or other user of the medical graft materials of the invention will prepare the wound for treatment in a conventional fashion, which may for example include cleaning and/or debridement of the wound with water, physiologic saline or other solutions, and potentially also treating the wound with antibiotics or other therapeutic agents. The medical graft construct of the invention will be applied to the wound in a fashion to facilitate and promote healing of the wound. In this regard, the inventive construct may be applied in a dehydrated, partially hydrated, or fully hydrated state. Once applied to a wound, the modified ECM graft material of the invention will hydrate (if not previously hydrated) and remain generally in place either alone or in combination with other wound dressing materials applied below or on top of the modified ECM material.

The invention also encompasses medical products that include a modified ECM graft material, or intermediate material, as described herein sealed within sterile medical packaging. The final, packaged product is provided in a sterile condition. This may be achieved, for example, by gamma, e-beam or other irradiation techniques, ethylene oxide gas, or any other suitable sterilization technique, and the materials and other properties of the medical packaging will be selected accordingly. In addition, the modified ECM graft materials may be packaged in a wet or dried state. In situations wherein sensitive growth factors or other bioactive proteins native to the ECM material or added as exogenous materials are present, terminal sterilization methods that result in the retention of substantial amounts of the original activity of these materials will be preferred. In these regards, in certain embodiments, packaged, modified ECM materials of the invention will be terminally sterilized using radiation such as E-beam, gas plasma (e.g. Sterrad), or hydrogen peroxide vapor processing.

All publications cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A medical graft product, comprising:
an extracellular matrix material retaining native heparin molecules, wherein the extracellular matrix material is substantially depleted of native heparin binding proteins and contains non-native heparin binding proteins bound to the native heparin molecules.

2. The medical graft product of claim 1, wherein the extracellular matrix material comprises submucosa, dermal collagen, dura mater, pericardium, or basement membrane.

3. The medical graft product of claim 2, wherein the submucosa comprises mammalian submucosa.

4. The medical graft product of claim 3, wherein the mammalian submucosa comprises porcine submucosa.

5. The medical graft product of claim 4, wherein the porcine submucosa comprises small intestine submucosa.

6. The medical graft product of claim 1, wherein the non-native heparin binding proteins include exogenous growth factors.

7. A medical graft product for healing a wound in a patient, comprising:
an extracellular matrix material; and
one or more exogenous growth factors, wherein the exogenous growth factors are bound to native heparin binding sites retained within the extracellular matrix material.

8. The medical graft product of claim 7, wherein the one or more exogenous growth factors comprise fibroblast growth factor, heparin binding epidermal growth factor (HBEGF), vascular endothelial growth factor (VEGF), placental growth factor (PIGF), heparin-binding EGF-like growth factor, transforming growth factor-beta (TGF-beta), interferon-gamma (IFN-gamma), platelet-derived growth factor (PDGF), pleiotrophin, interleukin-8 (IL-8), or any suitable combination thereof.

9. The medical graft product of claim 8, wherein fibroblast growth factor includes FGF-1 (aFGF), FGF-2 (bFGF), FGF-3, FGF-4, FGF-5, FGF-6, FGF-7, FGF-8, FGF-9, or any suitable combination thereof.

10. The medical graft product of claim 7, wherein the one or more exogenous growth factors facilitate a specific response in patient tissue.

11. The medical graft product of claim 7, wherein the extracellular matrix material comprises porcine extracellular matrix material and the one or more exogenous growth factors comprise human growth factors.

12. A medical graft product for facilitating the repair of patient tissue, comprising:

a collagenous material, wherein the collagenous material includes endogenous heparin molecules to which exogenous heparin binding proteins are bound, wherein the exogenous heparin binding proteins are effective to facilitate tissue repair.

13. The medical graft product of claim 12, wherein the collagenous material comprises an extracellular matrix material.

14. The medical graft product of claim 13, wherein the extracellular matrix material comprises a multilaminate extracellular matrix material.

15. The medical graft product of claim 13, wherein the extracellular matrix material comprises a sheet material.

16. The medical graft product of claim 12, wherein the exogenous heparin binding proteins comprise one or more human growth factors.

17. A medical graft product for tissue repair in a patient, comprising:

a sterile, remodelable, and collagenous extracellular matrix material retaining native heparin molecules and substantially depleted of native heparin binding proteins.

18. The medical graft product of claim 17, wherein the collagenous extracellular matrix material comprises small intestine submucosa.

19. A medical graft product for repairing patient tissue, comprising:

a collagenous remodelable material having native heparin molecules bound to non-native growth factors, wherein the collagenous remodelable material is porcine and the non-native growth factors are human.

* * * * *